(12) United States Patent
Samson et al.

(10) Patent No.: US 6,673,042 B1
(45) Date of Patent: Jan. 6, 2004

(54) EXPANDABLE VENOUS CANNULA AND METHOD OF USE

(76) Inventors: Wilfred J. Samson, 10161 Bubb Rd., Cupertino, CA (US) 95014; Brady Esch, 10161 Bubb Rd., Cupertino, CA (US) 95014; Michael J. Lee, 10161 Bubb Rd., Cupertino, CA (US) 95014; Janine Robinson, 10161 Bubb Rd., Cupertino, CA (US) 95014

( * ) Notice: Subject to any disclaimer, the term of this patent is extended or adjusted under 35 U.S.C. 154(b) by 0 days.

(21) Appl. No.: 09/447,457

(22) Filed: Nov. 22, 1999

(51) Int. Cl.$^7$ .............................................. A61M 29/00
(52) U.S. Cl. ........................ 604/104; 604/107; 606/191; 606/198
(58) Field of Search .............................. 604/264, 104–9, 604/266, 268, 523, 532, 536, 6.16, 507, 508, 509, 510, 164.1; 606/191, 194, 198

(56) References Cited

U.S. PATENT DOCUMENTS

| | | | |
|---|---|---|---|
| 4,808,163 A | | 2/1989 | Laub |
| 4,885,003 A | | 12/1989 | Hillstead |
| 4,921,484 A | | 5/1990 | Hillstead |
| 5,002,560 A | | 3/1991 | Machold et al. |
| 5,034,001 A | | 7/1991 | Garrison et al. |
| 5,180,368 A | | 1/1993 | Garrison |
| 5,263,963 A | | 11/1993 | Garrison et al. |
| 5,368,555 A | | 11/1994 | Sussman et al. |
| 5,449,372 A | * | 9/1995 | Schmaltz et al. |
| 5,456,667 A | | 10/1995 | Ham et al. |
| 5,762,624 A | * | 6/1998 | Peters |
| 6,270,490 B1 | * | 8/2001 | Hahnen ...................... 604/509 |
| 6,340,356 B1 | * | 1/2002 | Navia et al. ................ 604/104 |

OTHER PUBLICATIONS

David P. Bichell, MD, et al., Axilloaxillary Cardiopulmonary Bypass: A Practical Alternative to Femorofemoral Bypass. © 1997 by The Society of Thoracic Surgeons Published by Elsevier Science Inc., Page(s) 702–705.

Joseph F. Sabik, MD, et al., Axillary Artery: An Alternative Site of Arterial Cannulation for Patients with Extensive Aortic and Peripheral Vascular Disease, © 1995 by Mosby–Year Book, Inc., The Journal of Thoracic and Cardiovascular Surgery, pp. 886–891.

Nicholas T. Kouchoukos, et al., Perfusion for Thoracic Aortic Surgery, Section V. Clinical Application and Management of CPB, pp. 636–654.

* cited by examiner

*Primary Examiner*—Michael J. Hayes
*Assistant Examiner*—Catherine Serke
(74) *Attorney, Agent, or Firm*—Fulwider Patton Lee and Utecht, LLP

(57) ABSTRACT

The cannula of the present invention is useful for standard gravity drainage or vacuum assisted/suction drainage. The cannula of the present invention has a flexible shaft composed of a tubular body and an expandable scaffolding. The expandable scaffolding has a contracted position, facilitating insertion into a vessel and an expanded condition configured to allow optimal drainage in a vessel. The cannula is inserted into a vessel and navigated into an operative position within the patient's venous system. Once the cannula is in the proper position, the scaffolding is expanded either through passive, active, mechanic, hydraulic, pneumatic, thermal or electrical actuation. The cannula of the present invention is capable of expanding a collapsed vein to its normal diameter and/or capable of supporting the vein when suction is applied to the cannula to help increase fluid flow through the cannula.

7 Claims, 11 Drawing Sheets

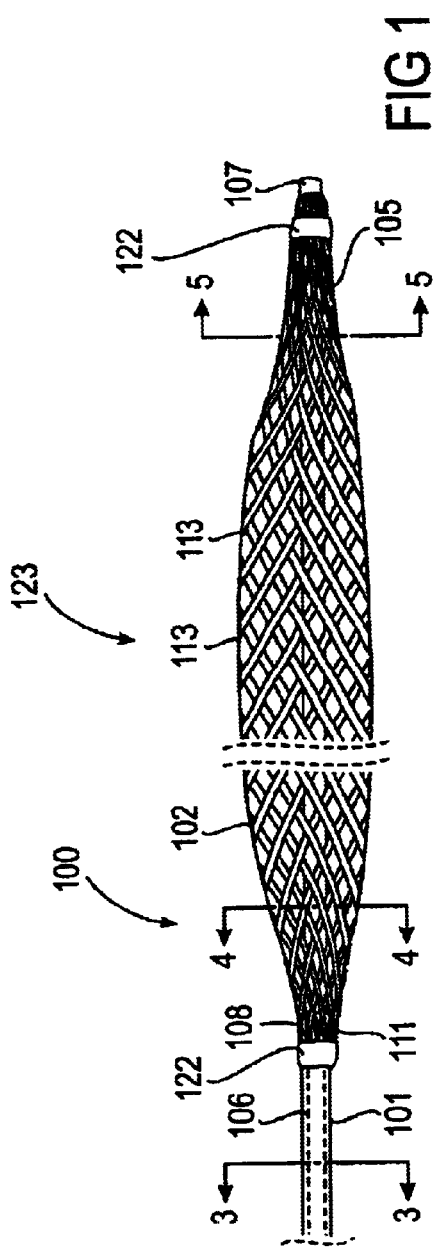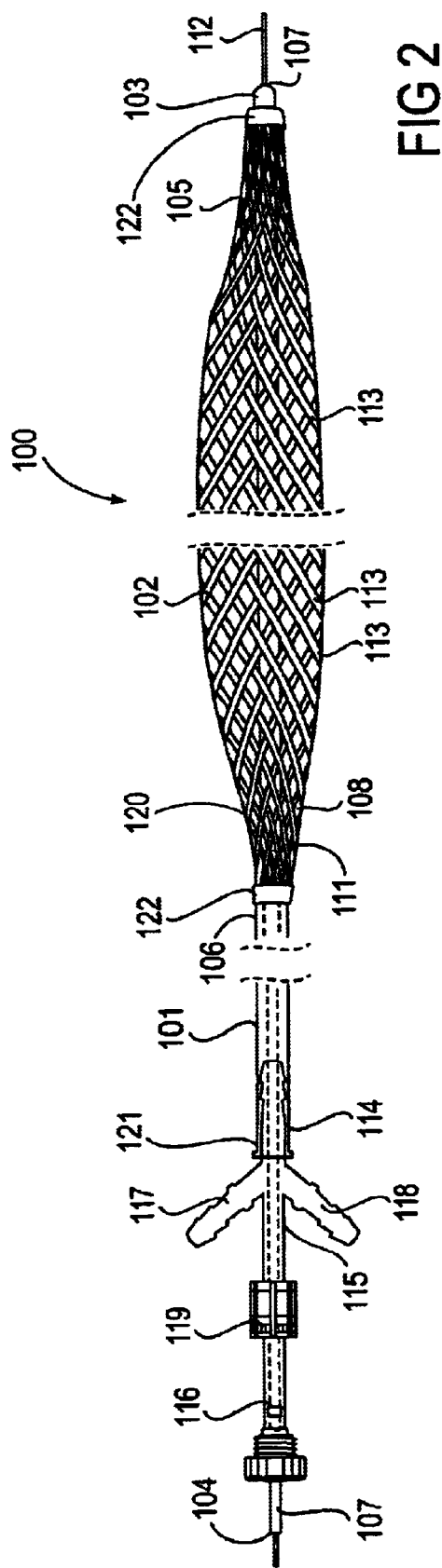

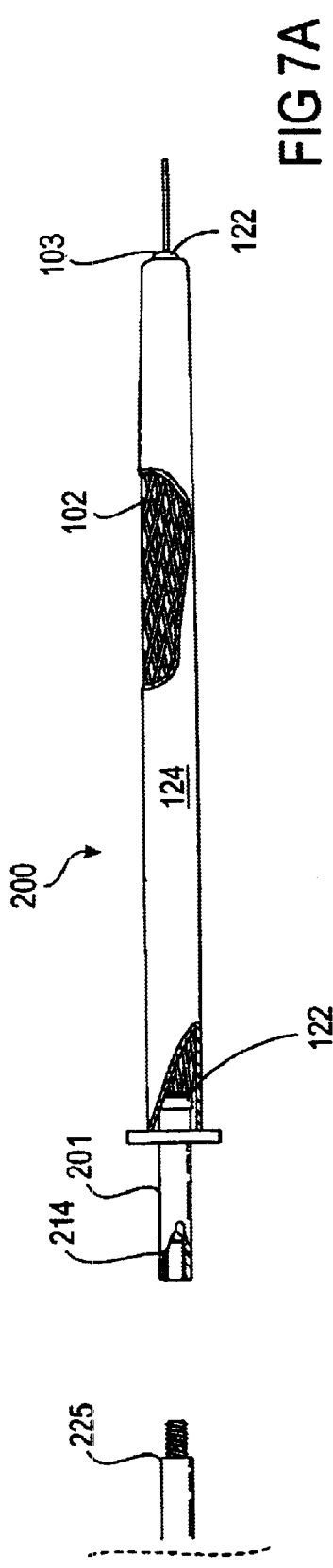
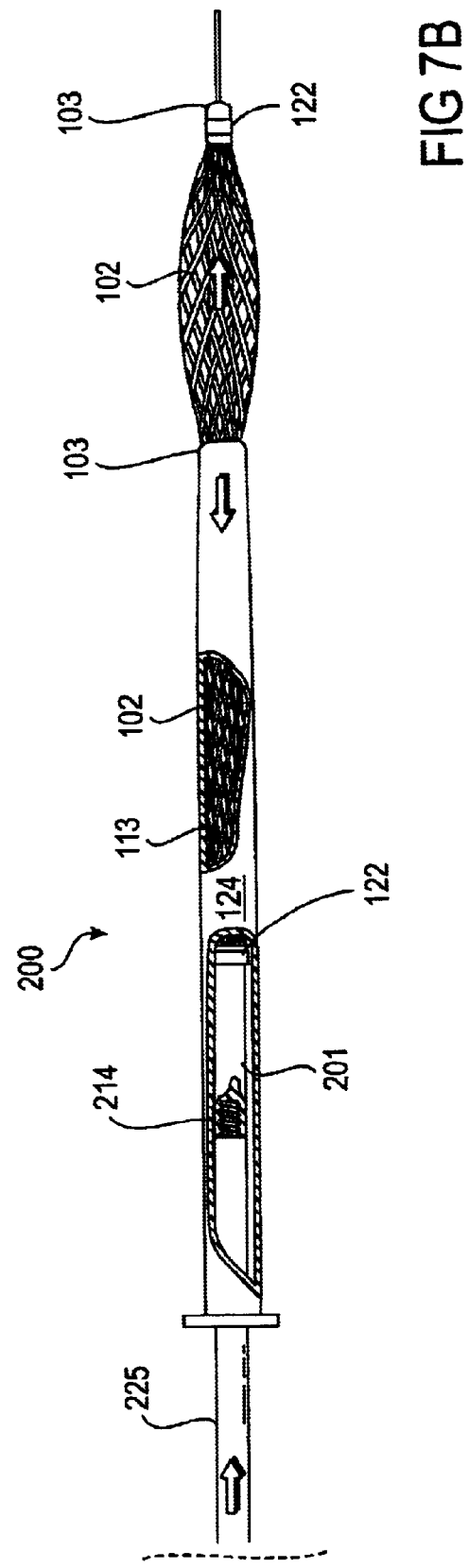

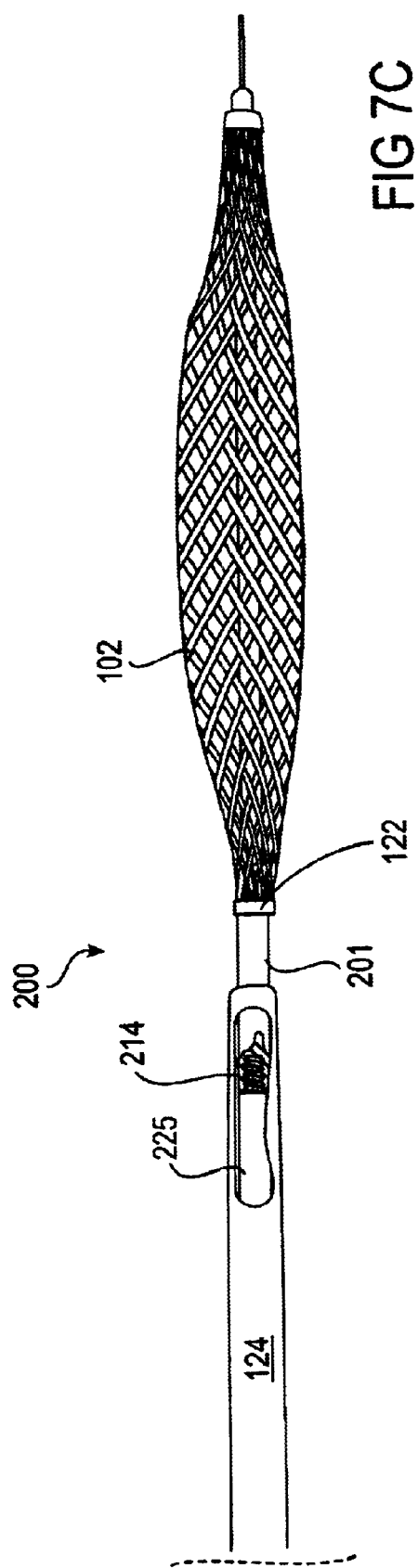
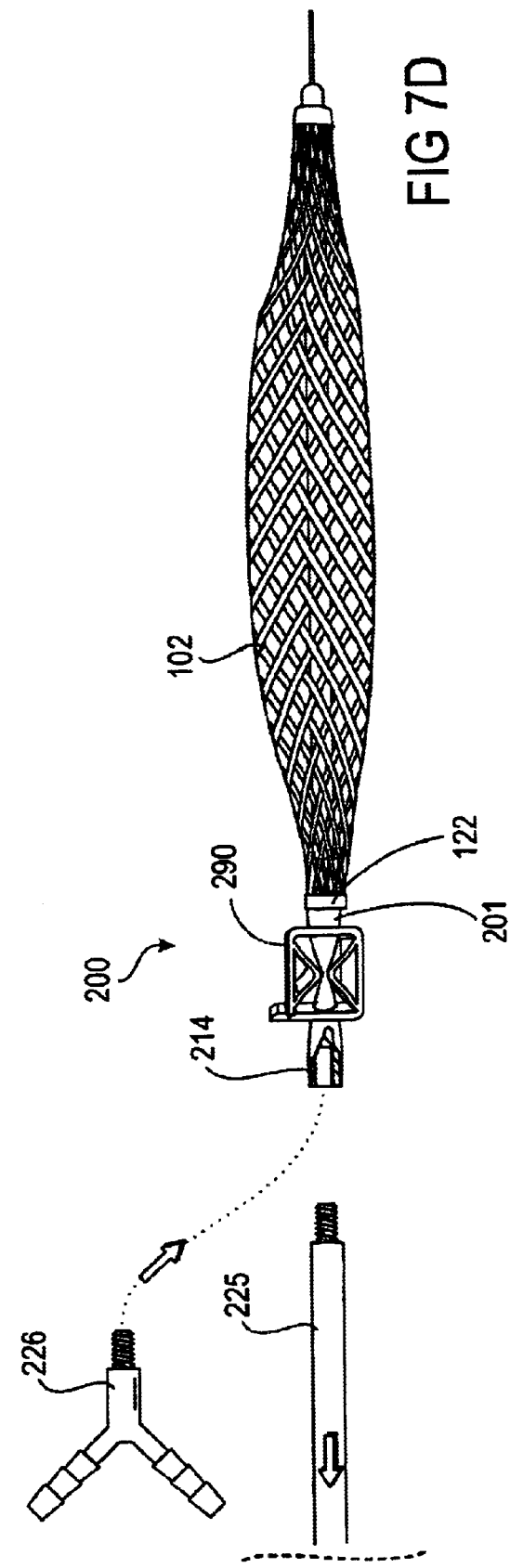

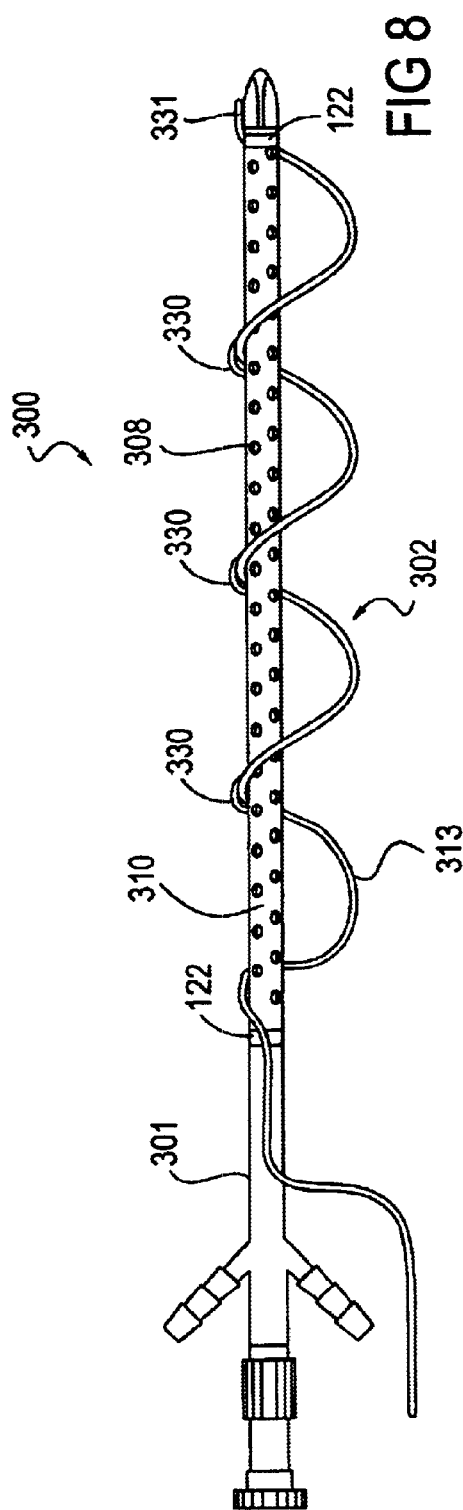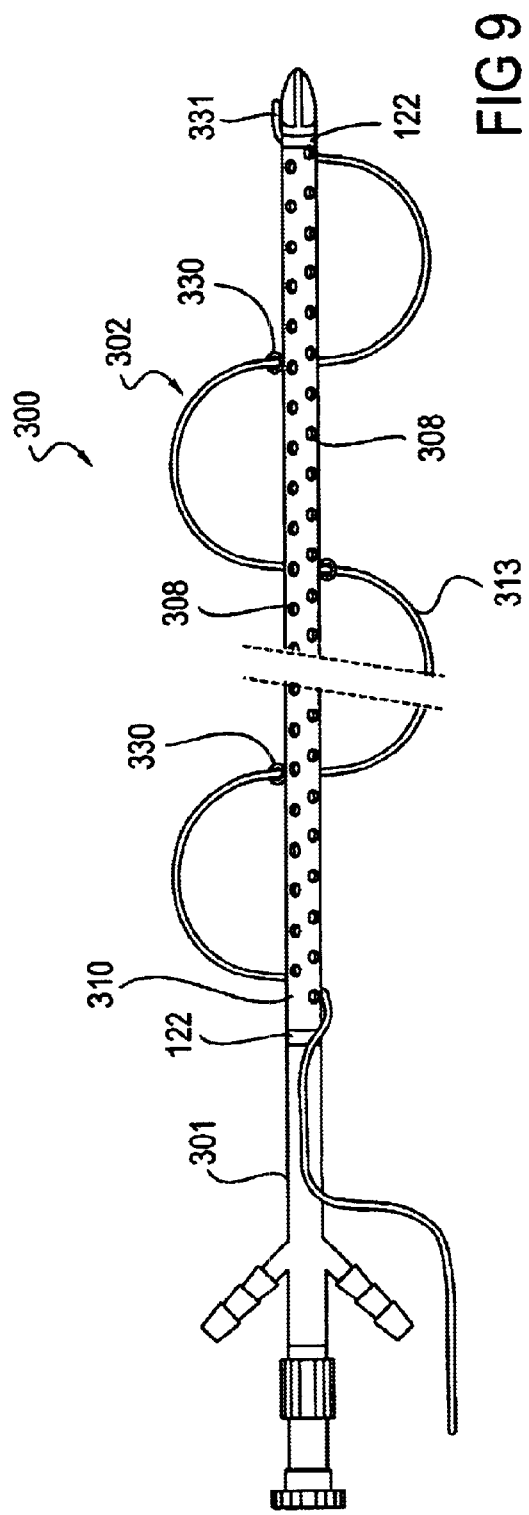

EXPANDABLE VENOUS CANNULA AND METHOD OF USE

FIELD OF THE INVENTION

The present invention relates generally to venous cannulae and catheters to be used during a medical procedure. More specifically, the present invention provides an improved cannula that is expandable from a contracted condition to an expanded condition to allow greater fluid flow in a vessel.

A venous cannula is provided having an expandable scaffolding that is configured for optimizing venous drainage during a medical procedure. In the collapsed position, the cannula scaffolding has a low profile especially suited for ease of entry into a vessel. In the expanded or deployed position the cannula scaffolding increases radially creating an area of free space between the catheter body and the vessel to optimize the fluid flow capacity of the catheter. The venous cannula of the present invention may be inserted from a peripheral vein such as the femoral, subclavian or jugular vein or alternatively may be used from a central approach into the right atrium, the superior vena cava, inferior vena cava or both.

BACKGROUND OF THE INVENTION

Over the past decades tremendous advances have been made in the area of heart surgery, including such life saving surgical procedures as coronary artery bypass grafting (CABG), cardiac valve repair or replacement and other surgical interventions. The development of cardiopulmonary bypass (CPB) has been a key technology making these advances possible. Performing heart surgery is a delicate operation requiring precise placement of sutures and incisions; therefore the majority of heart surgery is performed on an arrested or stopped heart. While the heart is arrested, systemic circulation is provided to the patient by using a cardiopulmonary bypass system or circuit. Typical bypass systems include: a venous cannula for withdrawing deoxygenated blood from the venous system, a venous reservoir for receiving the deoxygenated blood from the venous cannula, an arterial pump for circulating the venous blood from the venous reservoir to an integral heat exchanger and membrane oxygenator for conditioning the blood to the appropriate temperature and chemical composition and an arterial cannula for delivering the conditioned blood back to the patient. In addition, most extracorporeal circuits include a cardioplegia circuit or coronary circuit which performs the function of arresting the heart, as well as suction pumps for aspirating blood from the pericardial sac or in the pleural spaces through the use of a suction catheter, and/or to evacuate blood from the left ventricle by using a venting catheter.

Closed chest cannulation of the femoral artery and vein has also been practiced by physicians for the establishment of profoundly hypothermic total circulatory arrest and for reoperations with a high probability of entering a cardiac chamber during sternotomy. Even more recently, cardiac surgery has advanced to include a field of surgery called minimally invasive cardiac surgery. One specific type of minimally invasive cardiac surgery uses intercostal spaces to access a patient's heart and supplies the systemic circulation with oxygenated blood by using cannulas introduced into peripheral vessels. These procedures have helped reduce hospital recovery time by eliminating the more traumatic median sternotomy incision that is used in traditional heart surgery. However, since the cannulas used in these surgeries have smaller outside diameters, designed to enable introduction into peripheral vessels, there is a corresponding reduction or decrease in fluid flow through the internal lumens of these cannulas.

In more traditional CPB circuits, physicians typically place the venous reservoir at an elevation below the patient so that venous pressure and gravitational siphoning draw fluid through the venous cannula into the venous reservoir. This is problematic especially when using the peripheral cannulation technique since the cannula is much longer requiring more pressure to provide adequate fluid flow through the cannula. A second problem associated with using gravity, or siphoning is that the venous reservoir is limited in placement below body level, therefore more tubing is required to remove the venous reservoir out of the surgeon's way due to his location relative to the patient. This is disadvantageous since more tubing will require a larger amount of priming volume to fill the circuit which also clutters the surgical suite and makes the overall circuit less efficient.

Recognizing that gravity or siphon drainage may not always be sufficient to create adequate pressure for fluid withdrawal, especially in minimally invasive techniques, suction has been implemented as a means for increasing overall venous drainage. However, too much vacuum or suction results in the vein being collapsed down around the cannula shaft rendering the fluid drainage ports incapable of providing a passage way for fluid flow.

Another way physicians have tried to increase fluid flow through is to increase the diameter of the venous drainage cannula. One disadvantage to this solution is that a larger cannula shaft takes up more space in an already crowded surgical field and does not resolve the issue of minimizing priming volume. In addition, cannula size is limited in applicability based upon individual anatomy and the diameter of the vessel into which the cannula is to be inserted especially when using peripheral cannulation. Furthermore, cannulae having sufficient internal diameter to draw adequate blood flow are either so thin-walled that they are prone to kinking and collapse or are so thick-walled that they are not very flexible and have an overall diameter that is too large to be easily inserted into a peripheral vein.

Therefore, what has been needed and heretofore unavailable is a venous return cannula with a vacuum-controlled small reservoir or a special system that incorporates direct pumping from the venous cannula. Such a system creates a more compact circuit, requires less priming volume and is able to be located at the level of the operating table near the head of the patient. Furthermore, it would be advantageous to have a venous cannula that can be inserted either peripherally or centrally into the venous system of a patient at a minimum diameter that is capable of expanding to provide maximum fluid flow. The present invention solves these problems, as well as others.

SUMMARY OF THE INVENTION

In keeping with the foregoing discussion the present invention provides a venous drainage cannula for cardiopulmonary bypass that prevents vena cava collapse which can interfere with efficient venous drainage. The cannula of the present invention is useful for standard gravity drainage or vacuum assisted/suction drainage. The cannula of the present invention has a flexible shaft composed of a proximal tubular body and a distal expandable scaffolding. The expandable scaffolding has a contracted position, facilitating insertion into a vessel and an expanded condition configured for supporting the vessel to allow optimal flow. The cannula is inserted into a vessel and navigated into an operative position within the patient's venous system. Once the cannula is in the proper position, the scaffolding is expanded either through passive, active, mechanic, hydraulic, pneumatic, thermal or electrical actuation. The cannula of the present invention is capable of expanding a collapsed vein to its normal diameter and/or capable of supporting the vein when suction is applied to the cannula to help increase fluid flow through the cannula. Unlike conventional venous cannulae, whose drainage ports can become occluded when a vein collapses around the shaft, the cannula of the present invention has a scaffolding or permeable portion, which supports the vessel while suction or vacuum is applied to the venous cannula, and the drainage ports do not become occluded.

In a first illustrative embodiment, the venous cannula of the present invention has a cannula shaft with a tubular body, a scaffolding coupled to a distal end of the tubular body and an actuating member configured for expanding the scaffolding radially. The actuating member of this illustrative embodiment is in the form of a movable rod. To place the scaffolding in the contracted or insertion position, the actuating rod is moved in a distal direction contracting the scaffolding inward. To expand the scaffolding, the rod is moved in the proximal direction urging the scaffolding outward.

Coupled to the proximal end of the scaffolding is a tubular member having a proximal fitting coupled to a connection tubing in fluid communication with an extracorporeal circuit. In the expanded condition the scaffolding is sized and dimensioned to support the lumen of a vein allowing maximum diameter and flow of fluid into the tubular member and thereafter to the extracorporeal circuit. In addition, when necessary the scaffolding is designed to engage the vessel wall helping to keep the vessel in its natural condition when vacuum is applied. Alternatively, the expanded diameter of the scaffolding may be smaller than the vessel but is sized and dimensioned to keep the vessel from contracting beyond a certain diameter due to the rigid yet flexible characteristics of the scaffolding.

In a second illustrative embodiment, the venous cannula of the present invention has a cannula shaft with a tubular body, a shape memory scaffolding coupled to the distal end of the tubular body and an actuating member in the form of a movable sleeve. The sleeve is placed over the tubular member and the shape memory scaffolding to preloaded the scaffolding into the low profile insertion position. When the cannula is in the operative position, the sleeve is moved in the proximal direction, releasing the scaffolding, which automatically expands radially due to the shape memory properties of the scaffolding.

In a third illustrative embodiment one or more filament(s), wire(s), or strand member(s) are helically wound around the catheter to create an area of free space between the catheter and the vessel wall. The strand member is fixed at a distal portion of the tubular body. When the expandable venous catheter is placed in the operative position the proximal end of the strand member is advanced in the distal direction, urging the outward expansion of the strand member from the tubular body. The strand member can have a predetermined expansion diameter or alternatively may be configured to expand to a size equal to the internal surface of a vessel wall creating an area of free space between the tubular body and the vessel wall so that the ports do not become occluded by the vessel upon the application of suction.

In a fourth illustrative embodiment, the expandable scaffolding is comprised of supports, wings, standoffs, cones, or ribs, which are expanded by means of fluid inflation.

In a fifth illustrative embodiment the expandable venous catheter of the present invention is incorporated into a bypass system configured for differential perfusion. Methods of using the system and apparatus of the present invention are also disclosed. In order to further understand the features and functions of the present invention reference is made to the drawings and detailed description as set forth below.

BRIEF DESCRIPTION OF THE DRAWINGS

FIG. 1 is a side view of a shaft portion of an expandable venous catheter.

FIG. 2 is a side view of a venous catheter having an expandable scaffolding configured for maintaining optimal venous drainage during a surgical procedure.

FIG. 7A is a side view of a second embodiment of the present invention having a self expanding scaffolding in the contracted position with a sheath.

FIG. 7B is a side view of the expandable venous catheter of FIG. 7A with the sheath in an intermediate position allowing the self expanding scaffolding to be partially deployed.

FIG. 7C is a side view of the expandable venous catheter of FIG. 7A with the sheath completely withdrawn and the scaffolding completely expanded.

FIG. 7D is a side view of the expandable venous catheter of FIG. 7A illustrating the removal and coupling of the extension member and proximal fitting.

FIG. 8 illustrates a third embodiment of the present invention having a helically wound single strand member configured to hold the vessel away from the tubular member to allow optimal fluid flow.

FIG. 9 illustrates another variation of the present invention having a helically wound single strand member with alternating connection zones configured to hold the vessel away from the tubular member to allow optimal fluid flow.

DETAILED DESCRIPTION OF THE INVENTION

Figure 5:
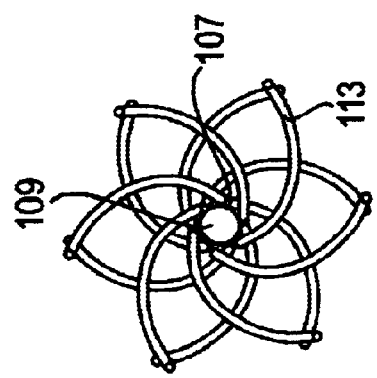
FIG. 5 is a magnified lateral cross section of the shaft portion of FIG. 1 taken along line 5—5 illustrating the shaft assembly and an exemplary lumen arrangement.

The venous cannula of the present invention is useful for standard gravity drainage or vacuum assisted suction drainage. The cannula has a flexible shaft composed of a proximal tubular body and a distal expandable scaffolding. The scaffolding can be actively or passively actuated from a contracted position to an expanded position and visa-versa. In addition, the cannula of the present invention is capable of expanding a collapsed vein to its normal diameter and/or capable of supporting the vein throughout a surgical procedure when suction is applied to the cannula to help increase fluid flow through the cannula. Unlike conventional venous cannulae, the scaffolding or permeable portion of the present invention allows for unimpeded venous return flow and supports the vessel while suction or vacuum is applied to the venous cannula.

The venous cannula of the present invention may be deployed passively or actively. For example, active deployment or actuation can be accomplished by using a mechanical, pneumatic, hydraulic, magnetic or electrical assembly. Alternatively, or in addition thereto, shape memory materials may be used to supplement or augment active actuating means by incorporating temperature sensitive materials such as NiTi or any other shape memory material that is elastic, superelastic or psuedoelastic. One means for combining active actuation means with passive actuation means is to use an actuating member, rod or sleeve in conjunction with a scaffolding having elastic, superelastic, pseudoelastic or any other shape memory property. In this variation of the invention, the scaffolding is placed in tension by extending the rod in the proximal or distal direction to place the scaffolding in tension. Subsequent to placing the scaffolding in tension, the actuating rod or member is released, allowing an increase in the radial expansion of the scaffolding by recalling a desired shape memory dimension. Alternatively, materials may be used that are sensitive to temperature, chemical or electrical manipulations such that the scaffolding may be deployed in a completely passive manner.

Referring more specifically to the figures where like reference numbers refer to like features or components, illustrated in FIG. 1 is a side view of a shaft portion 123 of a first embodiment of the venous cannula of the present invention that includes an expandable scaffolding 102 having a proximal portion 111 secured to a distal portion 106 of a tubular body 101. The shaft portion 123 as well as the scaffolding is broken to indicate that it is much longer than illustrated in connection with FIG. 1. The distal portion 105 of the scaffolding 102 is attached to a distal portion 120 of an actuating member 107. The actuating member 107, in this illustrative embodiment, is in the form of an actuating rod that expands and contracts the scaffolding 102 by adjusting the axial distance between the proximal portion 111 and the distal portion 105 of the scaffolding 102.

The scaffolding 102 may be constructed from spirally arranged, braided or coiled strand(s) or filament member(s) 113. Alternatively a single strand metal or filament fiber/member 113 may be used to achieve desired results. Alternatively, the scaffolding may be constructed from woven or knitted materials. The expandable scaffolding 102 may be attached anywhere along the length of the tubular member 101. In addition, the scaffolding 102 may be imbedded directly into the tubular body 101 or can be attached to the tubular body 101 by mechanical means. Furthermore, the scaffolding can be attached to a collar that is attached to the venous cannula 100 or have internal lumens in which the strand members 113 slide within the tubular body to actuate the scaffolding 102. Alternatively, a combination of passive actuation means through the use of shape memory materials may be used to augment the mechanical actuation means.

In the illustrative embodiment shown in FIG. 1 the scaffolding 102 is directly attached to a distal portion 106 of the tubular body 101 and a distal portion of the actuating member 107. The scaffolding 102 may be coupled to the actuating rod 107 by bonding the strand members 113 to the actuating rod 107 or through any other suitable means such as brazing, soldering, welding, coiling, embedding, adhesives, mechanical crimping or any other means commonly known in the art. The strand members 113 should have sufficient strength to support the vein during application of wall suction and should have sufficient flexibility to be navigated through the vein upon insertion.

The material used for the scaffolding 102 must be biocompatible, nontoxic and hemocompatible. An example of materials having these properties include, but are not limited to, polymers, elastomers, polymer or elastomer blends and copolymers, elastic or superelastic materials, alloys, metals, or temperature shape memory materials, such as a nickel/titanium alloy and composites or compounds or combinations thereof. Furthermore, the strand members 113 can have varying shape characteristics including, but not limited to, flat, round, square, triangular or elliptical forms in braids, coils or baskets and have the above described material compositions.

When using temperature sensitive shape memory material such as NiTi, transition temperatures should be chosen to be close to normal body temperature so that extreme temperature variations to recall the desired shape characteristics will not be necessary for the respective retraction or deployment of the strand members 113. One means for conferring a particular shape to a memory material is to anneal the wire members into a preferred position that represents the desired shape that is to be recalled at a later time. The shape memory material is cooled or warmed, above or below the transition temperature, (the temperature which induces the material to recall its preset shape memory). Depending on the transition temperature, this can be done at room temperature or in iced saline solution so that the expandable scaffolding 102 is malleable and can be shaped into a collapsed position. When the scaffolding is exposed to the predetermined transition temperature, for example body temperature, the scaffolding recalls the preset shape and conforms to that shape.

Shape memory alloys and the characteristics thereof are well known in the art and reference is made to U.S. Pat. No. 4,665,906 for a complete discussion of elastic, superelastic, pseudoelastic and temperature sensitive shape memory alloys; the complete discussion of which is herein incorporated by reference in its entirety. For illustrative purposes, the following is an example of a method of producing a self expanding, stainless steel, braided support having a stainless or stainless/platinum iridium core of one preferable size, alternatively larger and smaller sizes are within the scope of this invention. The wire shape, size and material components are preferably round 0.005 to 0.015" and made from 16 stainless steel 0.004×0.012", where the wires are braided onto a 0.625" polymer tubing. After the wires are braided around the polymer tubing, the polymer tubing is withdrawn and the braid wires are places into an annealing fixture that has the desired diameter, pitch, length, and shape. After the braided wires are placed in the annealing fixture the entire assembly is placed into a furnace set at 565° C. (1050° F.) for about 30 minutes. The assembly is removed from the furnace and is allowed to air cool or alternatively a vacuum furnace may be used with a programmable heat/cool profile for reliable process control to achieve the desired temperature transitions. This annealing process imparts a shape memory to the braid. After the annealing process is complete the wire braid is attached to a tubular delivery component for compressing the wire braid down, so that a sheath can be placed over the braid creating a compact profile. The braid is configured to allow a compressed size of <2.0 mm and an expanded size of >25.0 mm, with a foreshortening of about 50%. Expansion ratio vs. foreshortening can be optimized for the specific medical application and the preferred cannulation technique.

Alternatively, the self expanding braid may be constructed with 24.008" diameter wires, providing a compressed size of <5.0 mm and an expanded size of >30.0 mm with minimal foreshortening. For increased vessel coverage, more wires can be added. This set up can also be used in conjunction with active deployment mechanisms.

In addition, the expandable venous catheter 100 includes one or more markers, which may include radiopaque markers and/or sonoreflective markers, to enhance imaging of the expandable venous catheter using fluoroscopy or ultrasound, such as transesophageal echocardiography (TEE). Furthermore, it is desirable for the strand members 113 to be made of materials that have properties, which enable observation through flouroscopy or TEE. The wires may be made from radiopaque materials such as platinum-nickel alloy, platinum iridium, stainless steel, tantalum, gold or any other material having sufficient diameter in order to be observed within a patient by fluoroscopic examination. Alternatively, or in addition thereto, the strand members 113 may be coated with radiopaque materials, or the cannula may have radiopaque markers or ultrasound echogenic coating located on the shaft. In addition, the venous cannula 100 may be coated with heparin, activated plasminogen, phospholipids, hydrogels or any other coating that is antiadherent. In this illustrative embodiment, the expandable venous catheter 100 includes a distal radiopaque marker(s) 122 positioned near the distal portion of scaffolding and a proximal radiopaque marker 122 positioned near the proximal edge of the scaffolding 111. Each of the radiopaque markers 122 may be made of a ring of dense radiopaque metal, such as gold, platinum, tantalum, tungsten or alloys thereof, or a ring of a polymer or adhesive material heavily loaded with a radiopaque filler material.

Figure 6:
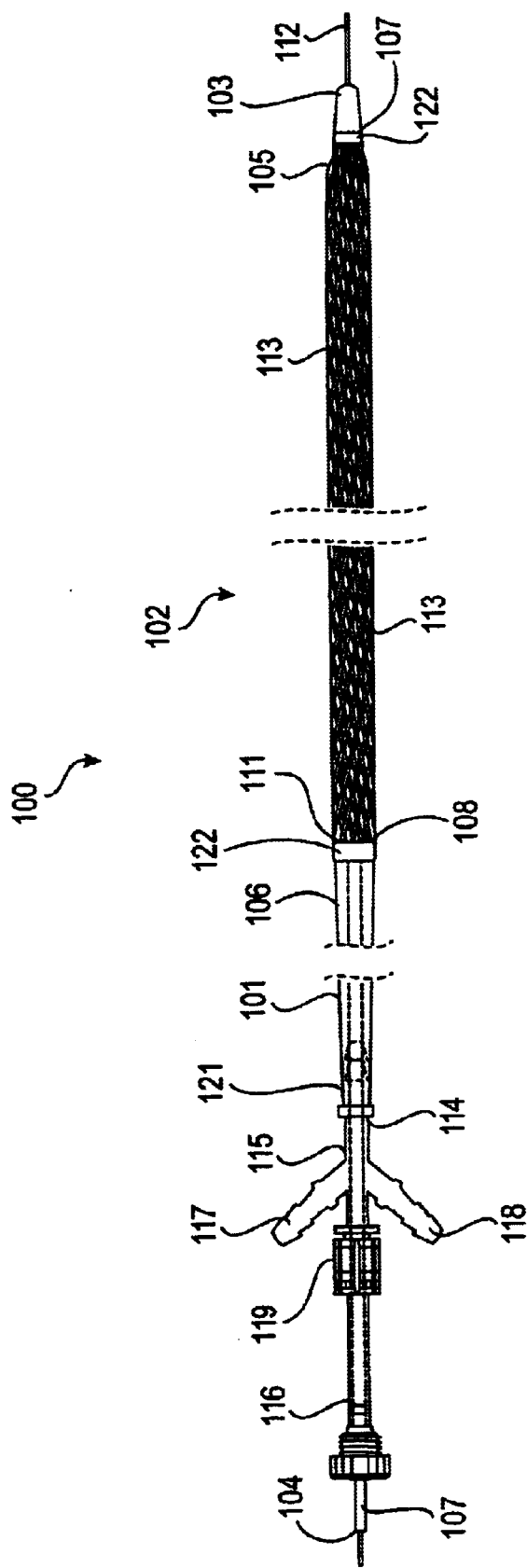
FIG. 6 is a side view of the venous cannula of FIG. 2 having a scaffolding in the contracted position.

Referring more specifically to FIGS. 2 and 6, the scaffolding 102 has an expanded condition, and a collapsed position. By moving the actuating member 107 in the distal direction, the angle of the strand members 113, relative to the longitudinal axis of the actuating member 107, decreases, urging the scaffolding into the collapsed position. In the collapsed position, the scaffolding 102 has a low profile and is not substantially larger than the diameter of the actuating member 107 or the tubular body 101 as illustrated in connection with FIG. 6.

Figure 3:
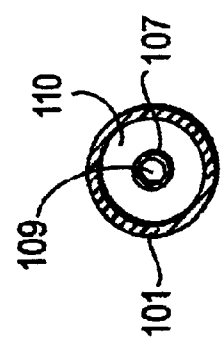
FIG. 3 is a magnified lateral cross section of the shaft portion of FIG. 1 taken along line 3—3 illustrating the shaft assembly and an exemplary lumen arrangement.

Referring now to FIGS. 2 and 3 the tubular body 101 has an opening coupled to a fitting 115 with multiple connectors whose functions will be discussed in greater detail below. The tubular body 101 is preferably extruded of a flexible thermoplastic material or a thermoplastic elastomer, including, but not limited to, polyvinylchloride, polyurethane, polyethylene, polypropylene, polyamides (nylons), PEBAX and alloys, metals, blends, or copolymers thereof, as well as braided, coiled or counterwound wire or filament reinforced composites or hypotubing.

Extending through the tubular body 101 is a fluid flow lumen 110. In alternative embodiments more than one fluid flow lumen can be provided. The fluid flow lumen extends from the proximal opening of the tubular body 101 to a distal portion 106 of the tubular body 101. The fluid lumen 110 is in fluid communication with a distal opening(s) 108 residing in the exterior of the tubular body 101 for receiving fluid.

Preferably, the tubular body 101 is of thin walled construction to maximize the internal diameter for a given outside diameter and length of the tubular body 101. Thin walled construction also allows the outside diameter of the tubular body 101 to be minimized in order to reduce the invasiveness of the medical instrument at the insertion site.

The tubular body 101 has a length sufficient to reach from a venous insertion access point while connected to an extracorporeal bypass circuit. For femoral venous deployment, the tubular body preferably has a length from approximately 40–150 cm, alternatively a short tubular body connected to suitable tubing could also be used such that a length of 1 cm to about 5 cm could also be used. The expandable scaffolding 102 in the unexpanded condition has approximately the same diameter as the tubular body 101 and may range from about 2.0 mm to 8.0 mm and have an expanded diameter of a range from about 20.0 mm to 30.0 mm. In addition, the fluid lumen 110 is sized and dimensioned to allow sufficient venous drainage without creating fluid retention in the venous system. In a preferred embodiment the diameter of the fluid lumen 110 is about in the range of 3.3 mm to 13.0 mm and is configured to allow flows of 0.2 L/min to 7.0 L/min.

The actuating member 107 is slidably disposed within the fluid lumen 110 and extends within the fluid lumen beyond the distal end of the tubular body 101. The position of the actuating member 107 within the tubular body 101 may be coaxial or, alternatively, slightly out of center. Preferably, the actuating member has a small outer diameter to maximize the amount of space for fluid communication within the fluid lumen 110. Furthermore, the actuating member 107 has sufficient column strength to actuate the expandable scaffolding 102 while having sufficient flexibility to be navigated through a vessel without damaging the internal vessel wall. The actuating member 107 may be extruded from a flexible thermoplastic material, or a thermoplastic elastomer. Alternatively, the actuating member can be made from stainless hypotube, NITINOL rod or tube, metals, solid metal polyvinylchloride, polyurethane, polyethylene, polypropylene, polyamides (nylons), and alloys or copolymers thereof, as well as braided, coiled or counterwound wire or filament reinforced composites or any material composition that is biocompatible and has sufficient column strength to actuate the scaffolding 102.

Figure 4:
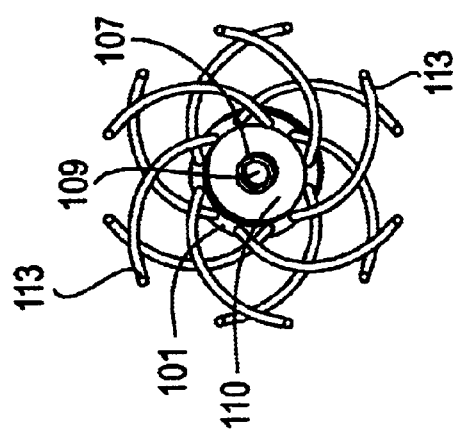
FIG. 4 is a magnified lateral cross section of the shaft portion of FIG. 1 taken along line 4—4 illustrating the shaft assembly and an exemplary lumen arrangement.

Referring now to FIGS. 3–5, the actuating member 107 has a guidewire lumen 109 which generally extends through substantially the entire length of the actuating member 107 from a proximal opening 104 in the exterior of the actuating member 107 to a distal port(s) 103 defined by the distal opening(s) of the actuating member 107 and is sized to receive a guidewire 112. A fixed guidewire, standard guidewire, stearable guidewire or any number of high performance torque guidewires can be implemented. One example of a movable guidewire to be used in the present invention is a movable guidewire preferably made of nested coil construction having two or more layered coils, which are coated with a polymeric material on the outside, such as teflon, polyurethane, parylene, hydrophillic coatings or the like.

The movable guidewire 112 is first positioned within the vascular system by way of the Seldinger technique with the use of a needle so that its distal end extends beyond the insertion site. The venous catheter 100 is then inserted over the movable guidewire 112 using the guidewire lumen 109 of the actuating member 107. Alternatively, a fixed guidewire may be secured to the distal end of the actuating member 107. In the fixed guidewire variations the catheter can be guided through the branches of the vascular network by rotating the entire catheter, causing the tip of the guidewire 112 to move into the desired area of the venous system.

Alternatively, the guidewire lumen 109 may extend from the distal portion of the elongated tubular body 101 from a proximal side opening in the sidewall of the tubular body 101 to a distal port in the distal end of the tubular body 101. A hemostasis valve 116 or other suitable sealing means is provided to prevent back bleeding out the proximal opening 104 of the actuating member 107. Alternatively, or in addition thereto, the guidewire lumen 109 may be configured to receive a stylet for percutaneous insertion into a vessel and to provide additional stiffness to increase the column strength of the actuating member 107. Alternatively, the guidewire lumen 109 may include an internal shoulder configured for receiving and engaging a stiffening rod to increase the rigidity and actuating efficiency of the actuating member 107. Alternatively, or in addition thereto, a second lumen may be provided within the actuating member 107 for insertion of a separate device to measure pressure, temperature and chemical composition in the venous system or a medical device to help position the catheter through transillumination, infrared light, optical fibers, echocardiography or sonar. The diameter of the guidewire lumen 109 should be sufficiently large to allow the catheter to be easily advanced and removed over the guidewire and be sufficiently large to accommodate a stylet, trocar for percutaneous insertion, or any other type of stiffening member.

Attached to the proximal end 114 of the tubular body 101 is a proximal fitting 115 with a series of connectors performing various functions. In this illustrative embodiment, the proximal fitting 115 has a barb connector 117 or other suitable fitting capable of being coupled to a CPB machine, a luer connector 118 for withdraing fluid samples or for the injection of therapeutic agents and other chemicals and a Thouy-Borst fitting 119 or other suitable hemostasis valve configured for maintaining a fluid tight seal and for receiving the actuating member or any other device. Referring to FIGS. 2 and 4 the fluid lumen 110 extends from an opening 121 through the tubular body 101 to a distal port(s) 108 at the distal end of the tubular body 101. Alternatively, the distal port(s) 108 may be proximal to the distal end and be in the form of a circular, square, triangular, rectangular or elliptical hole or holes or any other shape that facilitates the withdrawing of blood from the venous system. The guidewire lumen 109 extends from a proximal guidewire opening 104 to a distal guidewire port(s) 103.

The scaffolding 102 may be deployed passively, actively or a combination of both. For example, in the embodiment described above, the actuating member 107 may be used to supplement or augment passive actuating means by incorporating temperature sensitive materials such as NiTi or any other shape memory material that is elastic, superelastic or psuedoelastic.

FIGS. 7A through 7D illustrate a second embodiment of the present invention configured for peripheral insertion. In many respects this embodiment is similar in materials and construction to the previous embodiment, however in this illustrative embodiment the venous catheter 200 is deployed by actively withdrawing an outer tube or sheath 124 to release a self-expanding or passively expandable scaffolding 102. The outer tube 124 may be provided to cover the expandable scaffolding 102 to compress the scaffolding into a collapsed state and to provide a smooth outer surface for insertion and withdrawal of the venous catheter 200 preventing premature deployment of the venous scaffolding 102, particularly if passive deployment means are used, for example shape memory alloys. Suitable materials for the sheath include but are not limited to; thermoplastic elastomers such as, polyvinylchloride, polyurethane, polyethylene, polypropylene, polyamides (nylons), and alloys, metals copolymers or any combination thereof.

The venous catheter 200 is prepared for use by folding or compressing the expandable scaffolding 102 into a collapsed state within the outer sheath/tube 124. The scaffolding 102 is coupled to the tubular body 201 by any of the means described in connection with the previous embodiment. The tubular body 201 has a proximal opening 214 that is configured for receiving an extension member. In this illustrative embodiment the proximal opening 214 has a threaded portion which facilitates the coupling of an extension member/rod 225 or a proximal fitting 226 depending upon the current step of the medical procedure. Alternatively, no threaded portions may be used and the extension rod may be inserted directly into the tubular member 201 to accomplish an interference fit, snap fit or mechanical seal.

In use, the expandable venous catheter 200 is inserted into a vessel with the extension rod 225 coupled to the proximal opening 214 of the tubular member 201 as illustrated in FIG. 7A. The distal end 103 of the venous catheter 200 is inserted into a peripheral vein such as the femoral, illiac, subclavian or jugular vein in a retrograde fashion or alternatively through a central approach or intercostal space between the ribs. Preferably, this is done through a peripheral venous access site, such as the femoral vein, using the Seldinger technique or an arterial cutdown. The preloaded scaffolding 102 and sheath 224 are advanced up the femoral vein and into the right atrium while in the collapsed state. The position of the venous catheter 200 may be monitored using sonar, infrared, visible light, near infrared, fluoroscopy or ultrasound, such as transesophageal echography (TEE). Appropriate markers 122, which may include radiopaque markers and/or sonoreflective markers, may be located on the distal end 103. In this illustrative embodiment, the expandable venous catheter 100 includes a distal radiopaque marker 122 positioned near the distal portion of scaffolding 105 and a proximal radiopaque marker 122 positioned near the proximal edge of the scaffolding 111. Each of the radiopaque markers 122 may be made of a ring of dense radiopaque metal, such as gold, platinum/iridium, stainless steel, platinum, tantalum, tungsten or alloys thereof or a ring of a polymer or adhesive material heavily loaded with a radiopaque filler material. In addition, the scaffolding itself may be coated with sonoreflective or radiopaque materials.

When the distal end 103 of the catheter 200 is in the operative position, in the right atrium, superior vena cava, inferior vena cava, or in combination of more than one, the outer tube or sheath 224 is withdrawn and the scaffolding 102 is deployed. When the expandable venous catheter is navigated into the appropriate position with the distal portion of the scaffolding 105 residing in the right atrium, inferior vena cava, superior vena cava or in combination thereof, the sheath 224 is withdrawn in the proximal direction which allows the self expanding scaffolding 102 to open. FIG. 7B shows the sheath in an intermediate position illustrating either the removal of the sheath for deploying the scaffolding or alternatively the advancement of the sheath when the procedure is over and the expandable venous catheter is to be removed and collapsed into the sheath 124.

FIGS. 7C and 7D further illustrate the advancement or removal of the sheath 124 from the expandable venous catheter 200 and the coupling or removal of a proximal fitting 226 to the proximal opening 121 of the tubular body 201. The extension member 225 is of a length sufficient to enable the removal or placement of the sheath 124 over the scaffolding 102 while the expandable catheter 200 is in the operative position in a patient's anatomy. For example, by referring to FIGS. 7B through 7C the series of events that enable the removal or placement of the sheath over the expandable scaffolding is clearly illustrated. In FIG. 7B the sheath 124 is pulled in the proximal direction revealing a portion of the expandable scaffolding 102. The extension member is configured to be of sufficient length to enable the surgeon to hold the extension member 124 while withdrawing the sheath 124. In FIG. 7C the sheath 124 has been withdrawn in the proximal direction such that the tubular member 201 is exposed so that the surgeon is now capable of holding the expandable venous catheter 200 by the tubular body 201 to completely remove the sheath 124 from the expandable venous catheter 200. After the sheath 124 is completely removed the rod 225 is removed and hemostats, pinch clamps 290 or hand pressure keeps the tubular body 201 closed to prevent back bleeding as illustrated in FIG. 7D. After removal of the sheath 224, a Y-barb connector 226 or other suitable connector capable of being coupled to a CPB machine is coupled to the proximal opening 214 of the tubular body 201. Thereafter, suitable tubing is connected to the barb connector 226 and the CPB apparatus to complete the circuit. At the end of the surgical procedure, the tubular member 201 is pinched off, the Y-barb connector 226 is removed and the extension member 225 is again coupled to the tubular body 201 enabling the placement of the sheath 224 over the expandable scaffolding 102. Alternatively a peal way sheath may also be implemented.

FIG. 8 illustrates another embodiment of the present invention configured for achieving optimal venous drainage with the application of suction. In this illustrative embodiment, one or more filament(s) or wire(s) 313 are helically wound around the catheter 300 to create an area of free space between the catheter 300 and the vessel wall. The expandable venous catheter 300 has a tubular body 301 that may be reinforced with filaments, or wire reinforcement. The tubular body 301 has drainage ports 308 that are in fluid communication with a fluid lumen 310 and are sized and configured for the withdrawal of fluid. An expandable scaffolding 302, in the form of a strand member(s) 313, is helically wound around the tubular body 301 at one or more zones of attachment 330 on the tubular body 301. The strand member(s) in this illustrative embodiment are in the form of a superelastic or shape memory alloy wire(s). The strand member 313 is fixed at a distal portion 331 of the tubular body 301. When the expandable venous catheter 300 is placed in the operative position the proximal end of the strand member 313 is advanced in the distal direction, urging the outward expansion of the strand member 313 from the tubular body 301. The strand member 313 can have a predetermined expansion diameter or alternatively may be configured to expand to a size equal to the internal surface of a vessel wall creating an area of free space between the tubular body and the vessel wall so that the ports 308 do not become occluded by the vessel upon the application of suction.

The strand members 313, in this and in all embodiments previously described, may be coated with Teflon, hydrophilic or heparin coatings, or other materials that are hemocompatible and lubricious. In the current embodiment, Teflon coating is especially beneficial so that the strand member(s) 313 are able to glide or slide through the attachment zone(s) 330 with little frictional resistance. Depending on the size of the vessel, the strand or wire 313 diameter may be in the range of approximately 0.010" to 0.030" for larger vessels and 0.002" to 0.010" for smaller vessels.

The zone(s) of attachment 330 may be accomplished by using sutures, metal clips, or by passing the strand members in and out of internal lumens or through the internal fluid lumen 310 of the tubular body 301. The zones of attachment 330 include all types of bonding materials and adhesives and mechanical fasteners in the form of metal/polymer collars, rings, windings and others. If the zones of attachment 330 are all located on the same side of the tubular body 301 the catheter will be urged in the direction of the attachments as illustrated in FIG. 8. By alternating the positions of the zones of attachment 330 to opposite sides of the tubular body 301 the catheter 300 will be centered relative to the wire members 313 as illustrated in FIG. 9.

Figure 10:
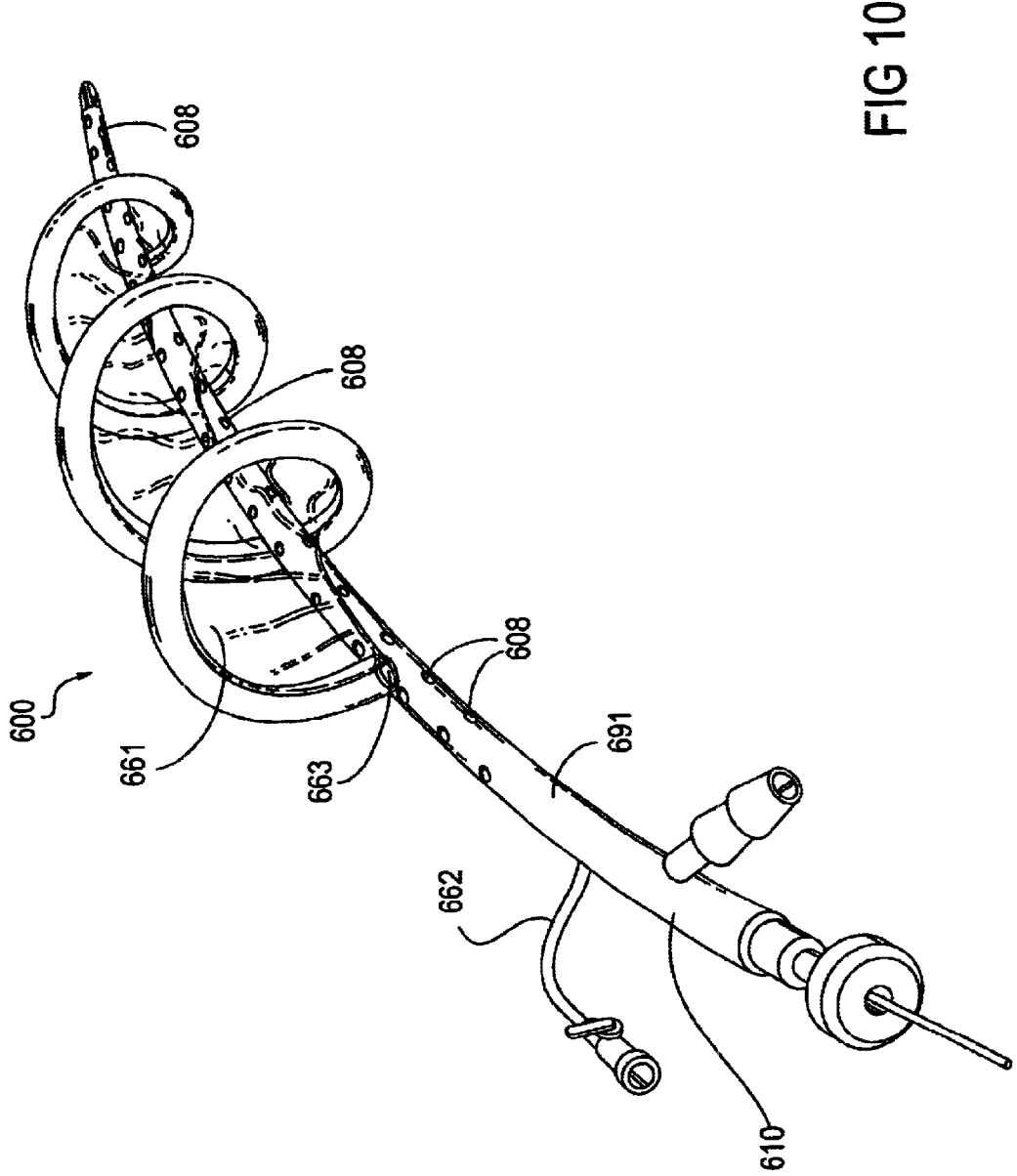
FIG. 10 illustrates a fourth embodiment of the present invention having an expandable scaffolding comprised of hydraulically actuated strand members with connected membranes.

FIG. 10 illustrates a fourth embodiment of the present invention having a hydraulically expandable helical wound scaffolding 600. The hydraulically wound scaffolding has an inflatable outer rim 660 that expands radially and hellically and an inner membrane 661 that attaches to the outer surface of the tubular body 691 and the inner surface of the outer rim 660. The outer rim 660 and inner membrane 661 may be made of the same materials or alternatively different materials. Furthermore, the outer rim 660 and inner membrane 661 may both be inflatable and built integrally or, alternatively, only the outer rim can be inflatable to create the desired characteristics and deployment. Materials that can be used for both the outer rim and the inner membrane include, but are not limited to, flexible thermoplastic materials, thermoplastic elastomers including but not limited to, polyvinylchloride, polyurethane, polyethylene, polypropylene, polyamides (nylons), polyesters, silicone, latex, C-FLEX, PEBAX and alloys, blends, or copolymers thereof.

The hydraulically or pneumatically expandable helical wound scaffolding 600 wraps around the tubular body when in the undeployed position and expands outward when an inflation medium such as saline solution, contrast medium or IC-Green is injected into an actuation lumen 662 in fluid communication with actuation port(s) 663 in fluid communication with the outer rim 660. The auger or corkscrew configuration is especially beneficial in that it provides support for the vein during suction, allows an area of free space to prevent occlusion of the venous ports 608 residing in the exterior of the tubular body 691 and allows fluid to drain in the proximal direction relative to the tubular body 691 such that all the venous drainage ports 608 along the length of the tubular body are utilized. The venous drainage ports 608 are in fluid communication with a 101 fluid lumen 610 residing within the tubular body 691 which transports the fluid to an extracorporeal circuit with the assistance of vacuum or suction. The membrane 661 can be made of a permeable material, having windows that allow fluid to flow therethrough, may be made of filaments, strands or wires or may be completely impermeable. Furthermore, the membrane 661 can serve as a means for limiting the outward expansion of the outer rim by being constructed of material less compliant than the outer rim 660 thereby giving more structural integrity to the overall scaffolding 600.

Figure 11:
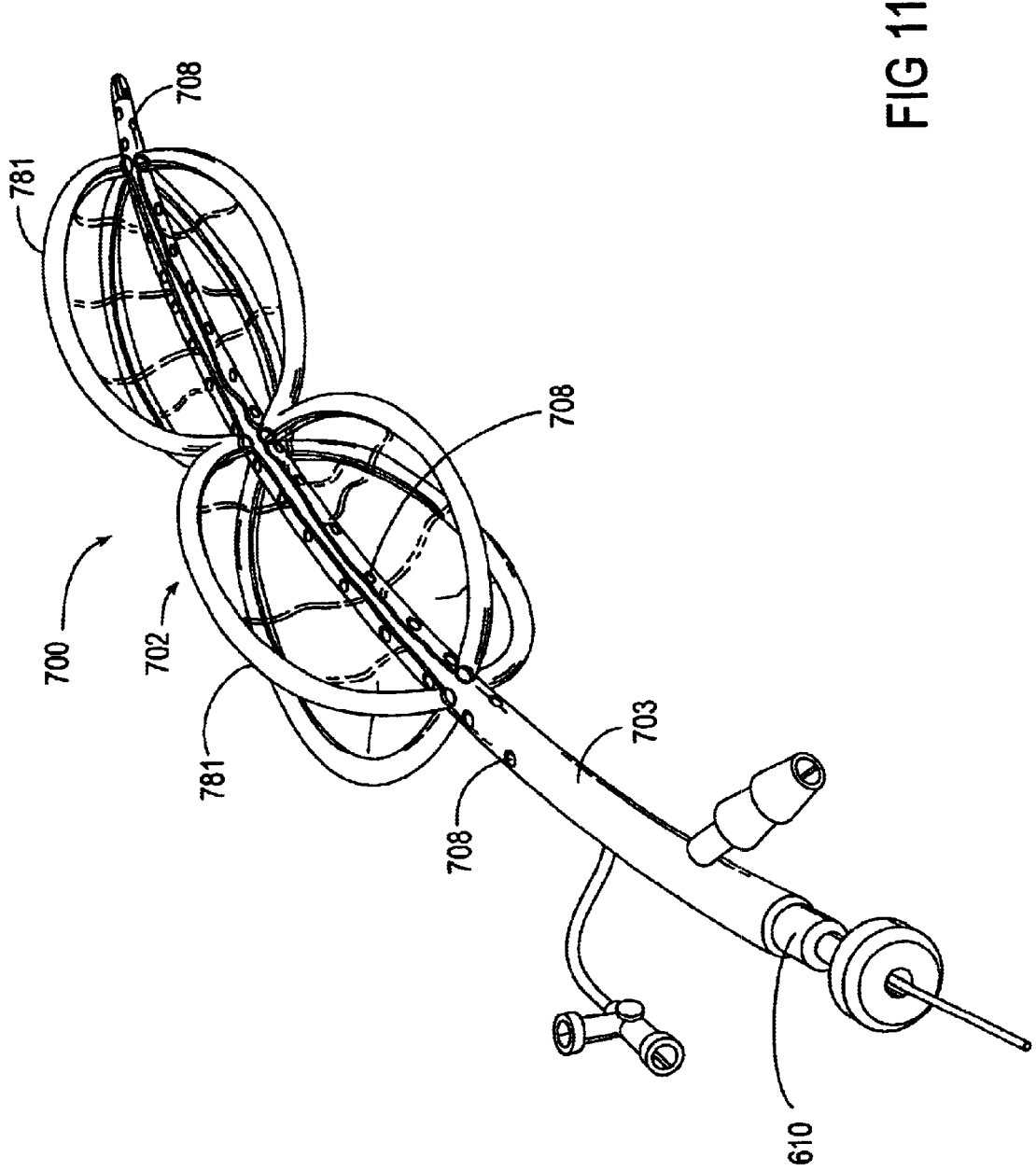
FIG. 11 illustrates a fifth embodiment of the present invention having an expandable scaffolding in the form of inflatable wings or struts.

FIG. 11 illustrates a fifth embodiment of the present invention having an expandable scaffolding 702 in the form of an inflatable wing or wings 781. In one preferred embodiment 1 to 30 wings 700 extend in parallel and circumferentially disposed along the length of the tubular body 703 to allow for optimal venous drainage through the venous drainage ports 708. The wings 781 are generally arcuate in shape and are constructed from various materials, such as a thin polymer film, for example polyurethane or polyethylene, although any number of shapes are conceivable to perform to desired results. Illustrated in FIG. 11 is a design having wings 781 which expand approximately perpendicular relative to the center axis of the tubular body 703. Alternatively, the wings 781 could have a curvature or other form to allow for more support. Furthermore, the wings 781 may have filament reinforcement or may have wire struts to aid in support. Cutouts or windows in the wings 781 can allow for better blood movement around or through the wings 781. At a given cross section, as many as four support wings stem from the central tubular member 703. The wings 781 are made from heat sealing polyurethane film, 0.002" thick, into wings that have a height of 5 to 15 mm each. Thinner material can be used as well as larger wings can be created. The wings 781 may have supports or tack points along its body to allow for better shape retention.

The device 700 will be inserted in the collapsed/non-inflated state. The device 700 may be fluid prepped to remove air from the wings. The device 700 may also be inserted with vacuum applied. Upon correct positioning, the device will be inflated with an inflation medium such as saline solution, contrast medium or IC-Green. The inflation medium may also be radiopaque, or alternatively or in combination therewith, radiopaque markers may be on the device to confirm positioning. Prior to removal, the inflation medium should be evacuated from the wings 781.

Figure 12:
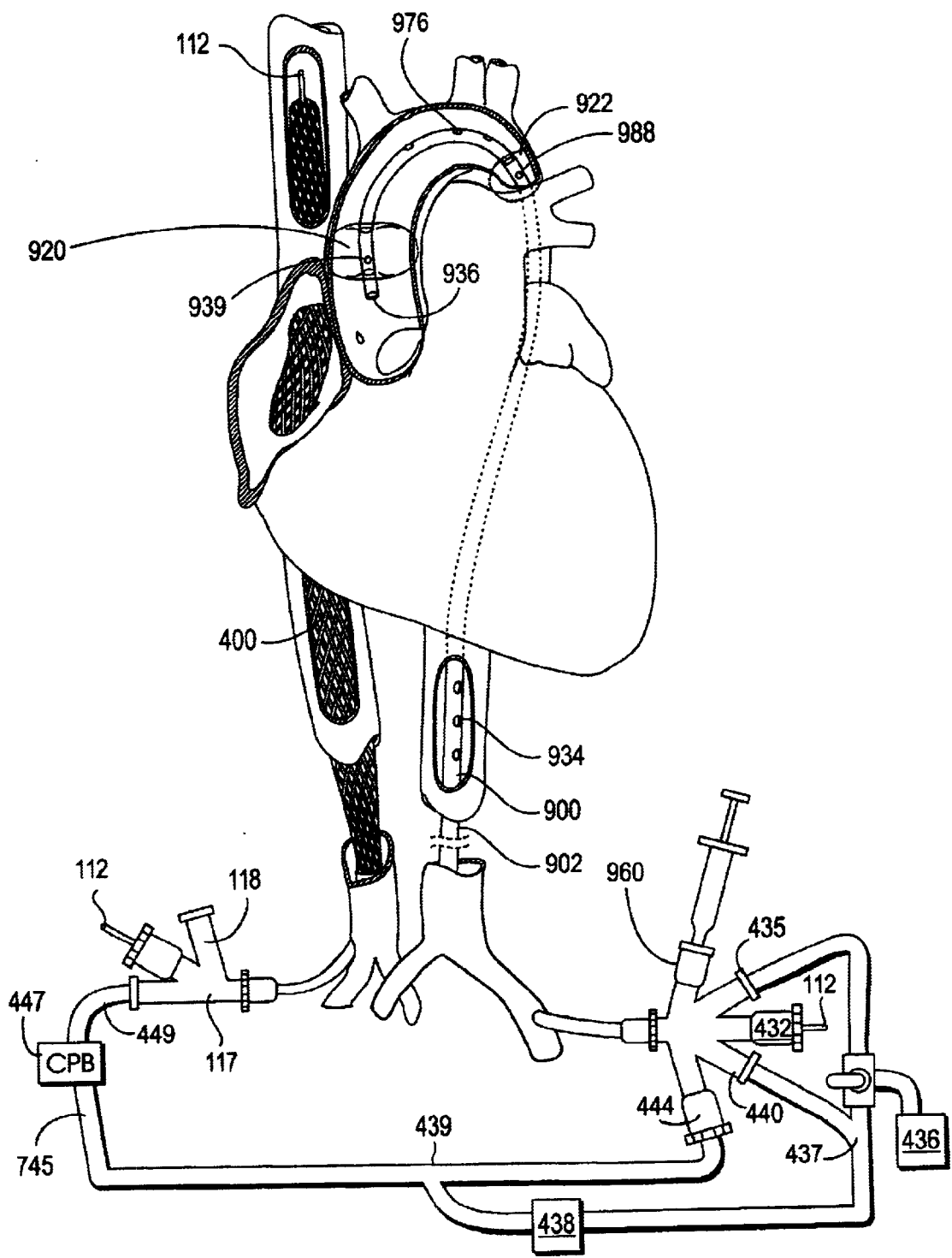
FIG. 12 illustrates the expandable venous catheter of the present invention deployed in a patient's venous system.

FIG. 12 illustrates the expandable venous catheter 400 of the present invention incorporated into a system to perform CPB. Any of the above described catheters can be used in the present system, however for ease of illustration, the expandable venous catheter associated with FIGS. 1 through 6 will be described in this illustrative embodiment. The expandable venous cannula 400 of the present invention can be used in standard open chest procedures as well as in minimally invasive procedures. When performing minimally invasive surgical techniques peripheral access to the venous system can be accomplished through any peripheral vein including the internal jugular, subclavian, iliac or femoral vein. In this embodiment of the invention, the venous cannula 400 is used in conjunction with a dual-balloon, selective arterial perfusion cannula 700 which shall be described in more detail below.

One method of using the venous drainage catheter 400 of the present invention is to insert the venous catheter 400 into a peripheral artery by way of the Selidinger technique or by cutdown. By way of example, FIG. 12 illustrates the expandable venous catheter 400 introduced into the right femoral vein. For femoral approaches, the length of the catheter is preferably about 40 cm to approximately 140 cm, more preferably 60 cm to approximately 120 cm. In alternative approaches, the jugular or subclavian veins may be utilized. For jugular or subclavian approaches the distance to be traveled into or through the right atrium is shorter than in the femoral approach, preferably having a length of about 20 cm to approximately 80 cm, more preferably about 40 cm to approximately 60 cm.

After insertion, the expandable venous catheter 400 is navigated transluminally into the inferior vena cava, right atrium and/or superior vena cava. Proper position can be established through any of the aforementioned techniques such as flouroscopy or ultrasound. After proper position is established, the scaffolding 102 is allowed to expand radially to a predetermined diameter or alternatively to a size that is equal to the interior surface of the vein. After the extracorporeal circuit has been properly primed CPB is initiated. To enhance venous drainage, the extracorporeal circuit is provided with vacuum assist or a suction pump.

The fluid lumen 110 of the expandable venous cannula is in fluid communication with distal port(s) 108 for receiving fluid from the right atrium, inferior vena cava and/or superior vena cava. The proximal portion of the venous cannula is connected to a fitting 115 with various connectors serving a multitude of functions. A luer connector 118 is provided for the withdrawal of fluid samples to determine chemical composition, temperature and pressure in and around the venous catheter 400. A Touhy-Borst fitting 119 or other suitable hemostasis valve configured for receiving a guidewire 112 or other medical device, and a barb connector 117, is connected to inflow tubing 449 for receiving fluid from the fluid lumen 110 which is communicated to a blood circulation pump 447. Fluid from the venous system is drained into a venous reservoir and into a combined heat exchanger/membrane oxygenator 447. After the blood is conditioned to the appropriate temperature and chemical composition, it is pumped by a centrifugal or roller pump to outflow tubing 745 which has a Y-connector 439 for separating the oxygenated blood into a corporeal branch and an arch branch which will be delivered through a dual balloon arterial cannula 900.

The dual-balloon, selective arterial perfusion cannula 900 is configured for peripheral insertion by way of the femoral artery. For a complete description of dual balloon selective arterial cannulae configured for use in the present invention reference is made to U.S. Pat. Nos. 5,383,854, 5,820,593 and 5,906,588 to Safar et al., and U.S. Pat. No. 5,738,649 to Macoviak and U.S. Pat. Nos. 5,833,671 and 5,827,237 to Macoviak et al., the complete disclosures of which are herein incorporated by reference in their entirety. The arterial cannula segments the aorta into a myocardial circulation, a corporeal circulation and an arch circulation by utilizing occlusion members, which at least in part partition the aorta. The arterial cannula has a tubular shaft 902 that includes a corporeal lumen, an arch lumen, a guide wire cardioplegia lumen, and a balloon inflation lumen. An upstream occlusion balloon 920 or other expandable occlusion member is mounted on the tubular shaft 902 so that it is positioned in the ascending aorta between the coronary arteries and the right brachiocephalic artery when in the operative position. A downstream occlusion balloon 922 or other expandable occlusion member is mounted on the tubular shaft 902 so that it is positioned in the descending aorta downstream of the left subclavian artery when in the operative position. The corporeal perfusion lumen extends through the tubular shaft 902 from a corporeal barb connector 444 to one or more corporeal perfusion ports 984 on the tubular shaft 902 proximal to the downstream occlusion balloon 922. The arch perfusion lumen extends through the tubular shaft 902 from an arch barb connector 440 to one or more arch perfusion ports 976 on the tubular shaft 902 between the upstream occlusion balloon 920 and the downstream occlusion balloon 922. The guidewire cardioplegia lumen extends through the tubular shaft 902 from a Y-connector to one or more cardioplegia ports 936 on the tubular shaft distal to the upstream occlusion balloon 920. The balloon inflation lumen extends through or along the tubular shaft 902 from a balloon inflation fitting 960 to a first balloon inflation port 988 within the downstream occlusion balloon 922 and a second balloon inflation port 730 within the upstream occlusion balloon 989.

Blood designated to be sent to the arch branch is cooled or warmed or chemically altered through a second blood conditioning device 438 and delivered to the arch lumen by way of the arch barb connector 440 and out arch ports 976 to provide cerebral protection. A second Y-connector 437 is provided in order to provide blood cardioplegia from a blood cardioplegia source 436 connected to the guidewire cardioplegia fitting 435. Blood designated for the corporeal circulation is delivered to the corporeal lumen by way of a corporeal barb connector 444 attached to the arterial cannula 900.

Figure 13:
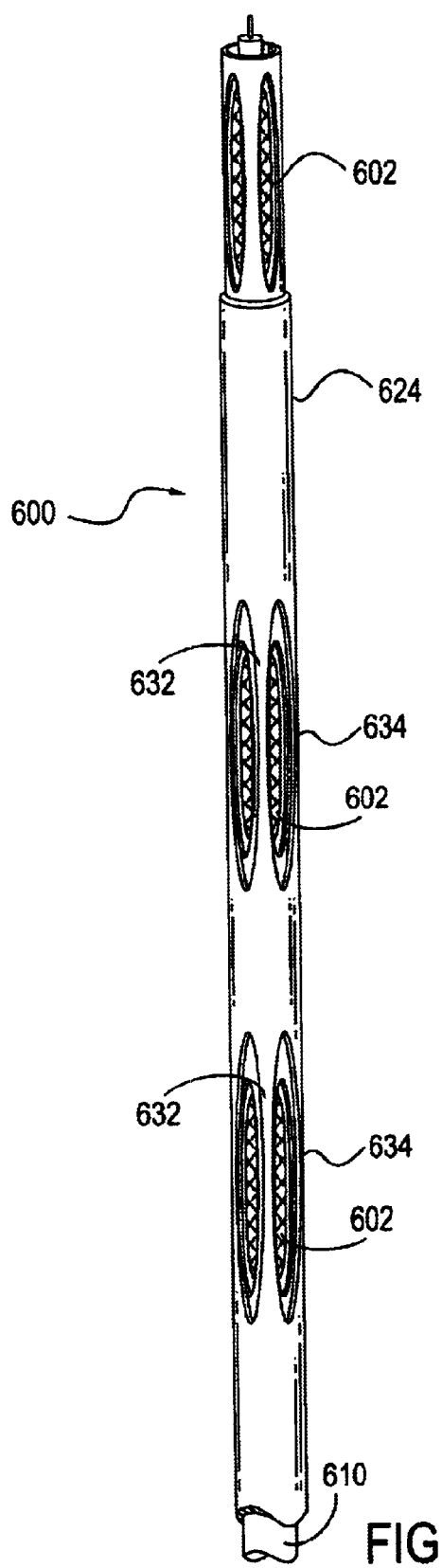
FIGS. 13–15 illustrate an expandable venous cannula having a sheath with intermittent windows.
Figure 14:
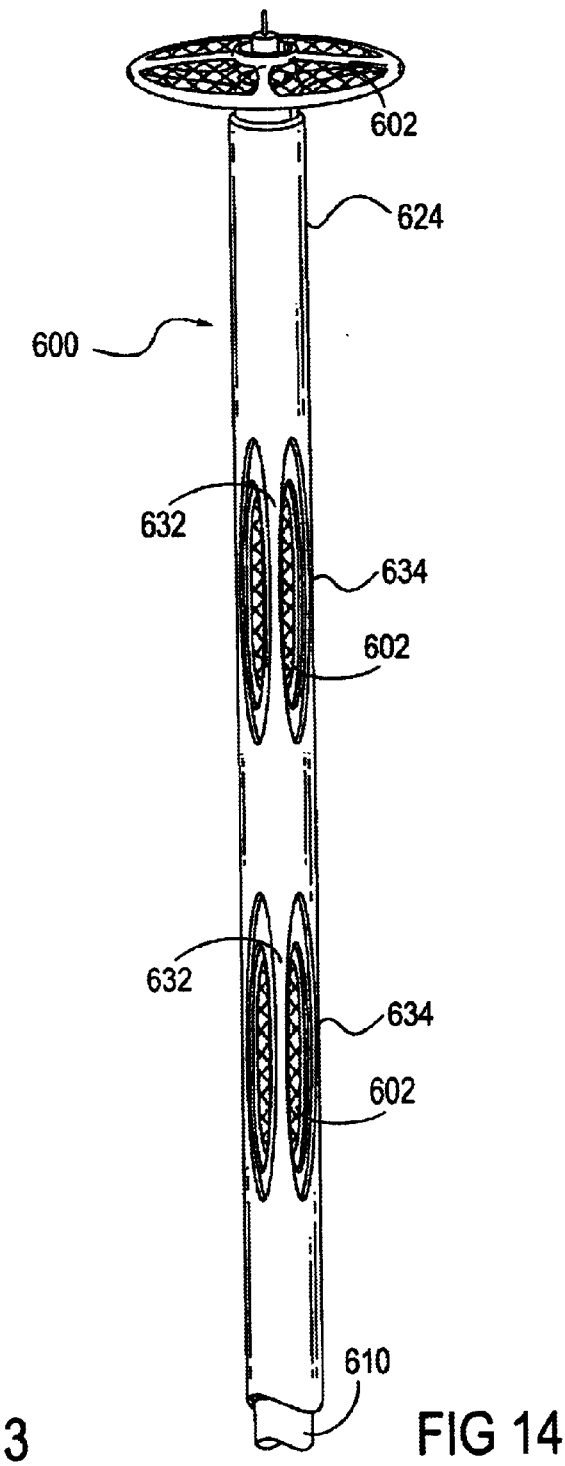
Figure 15:
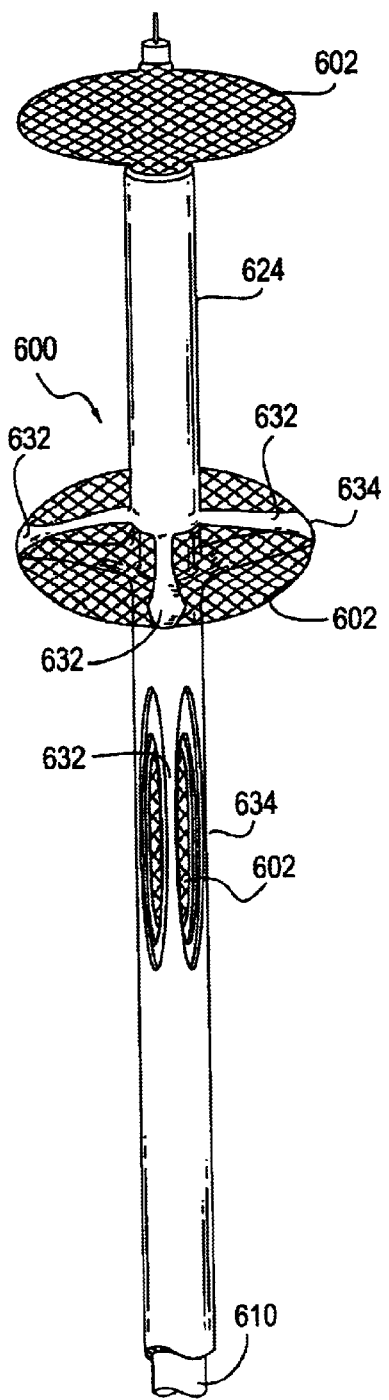

FIGS. 13–15 illustrate a sixth embodiment of the present invention having an expandable venous catheter 600 that is similar in materials and construction to the previous embodiment described in connection with FIGS. 7A through 7D, however in this illustrative embodiment the outer tube or sheath 624 has intermittent window(s) 634 which allow the expandable scaffolding 602 to expand radially outward. The windows 634 have longitudinally extending connective member(s) 632 which are flexible and are configured to expand radially when the expandable scaffolding 602 expands radially with or through the windows 634. The connective members 632 in this illustrative embodiment are arranged along the exterior of the sheath 624 and create a generally elliptical or spherical shaped window 634, however any shape can be used including squares, circles, octagons or any other shape that is conducive to facilitate the withdrawal of blood. The expandable scaffolding 602 may be self-expanding or manually, electrically or pneumatically actuated. In this illustrative embodiment, the outer tube or sheath 624 is provided to cover the expandable scaffolding 602 and to compress the scaffolding into a collapsed state and to provide a smooth outer surface for insertion and withdrawal of the venous catheter 600, thereby preventing premature deployment of the venous scaffolding 602, particularly if passive deployment means are used, for example shape memory alloys. The windows 634 are beneficial since they are spaced at a distance that allows minimal movement of the sheath 624 in the proximal or distal direction in order to have expansion of the scaffolding 602. The windows may be spaced apart by a distance approximately 5 mm to 30 mm or approximately about 10 mm to 70 mm. In addition, the plurality of windows may be 1 or as many as 50.

Figure 16:
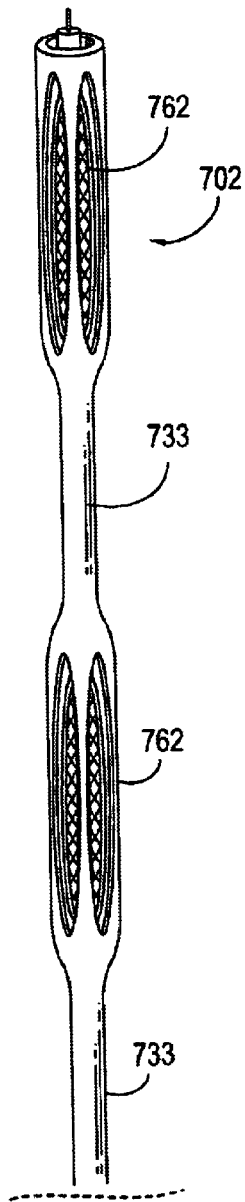
FIG. 16 illustrates and expandable scaffolding having solid support structures.
Figure 17:
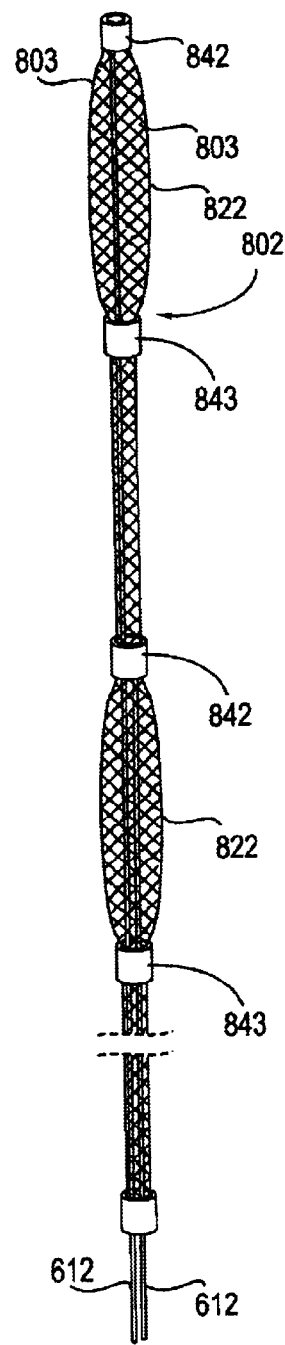
FIG. 17 illustrates an expandable scaffolding having movable couplings.

As can bee seen by referring to FIGS. 16 and 17 two variations of the expandable scaffolding are illustrated which can be used with the window sheath 624 of FIGS. 13–15. Alternatively, the expandable scaffoldings of the previous embodiments can also be used with the present embodiment. FIG. 16 illustrates the expandable scaffolding 702 having solid support structure(s) 733 residing between intermittent expandable baskets 762. The solid support structures may be made of copolymers, polyurethane, polyethylene, polypropylene, metals, alloys and any combination thereof. The expandable scaffolding 702 is actuated as one complete unit by moving the scaffolding 702 in the proximal or distal direction relative to the sheath 624. When the baskets 762 are moved to the appropriate position aligned with the windows 634, radial expansion occurs with or through the window 634. Upon radial expansion, blood or other fluid is allowed to flow through the window(s) 634 and through a fluid lumen 610 residing within the interior of the expandable venous catheter and to a blood conditioning apparatus.

FIG. 17 illustrates an expandable scaffolding 802 that is similar in materials and construction to that of FIGS. 1–6 however in this illustrative embodiment a series of expandable baskets 822 can be actuated simultaneously or in a staged fashion, or alternatively each basket 822 can be actuated selectively by using a single or multiple actuation member(s) 612. The scaffolding is constructed with a series of stationary couplings 843 and slidable couplings 842. When the actuating member 612 is pulled or shifted in the proximal direction, the slidable couplings 842 are moved in the proximal direction while the stationary couplings 843 remain in a constant position relative to the slidable couplings 842 urging the expandable scaffolding 802 and baskets 822 radially outward. Each of the slidable couplings 842 can be attached to an independent actuating members 612 or alternatively a single actuating member 612 can actuate all of the expandable baskets 822 by soldering the slidable couplings and strand members 803 to the actuating member 612.

Referring again to FIG. 14 the expandable scaffolding 602 may expand radially in a generally planar configuration or alternatively may be more radially elliptical in the horizontal plane relative to the catheter shaft illustrated in FIG. 15. FIG. 17 illustrates the expandable scaffolding 802 with a generally elliptical shape in the vertical position. The expandable scaffolding can have an expanded length greater than the expanded width or alternatively, the expandable scaffolding can have an expanded width greater than the expanded length.

Suitable materials for the sheath include but are not limited to; thermoplastic elastomers such as, polyvinylchloride, polyurethane, polyethylene, polypropylene, polyamides (nylons), and alloys, metals copolymers or any combination thereof. Of primary importance is that the sheath be constructed of materials that allow for expansion with or through the windows but have sufficient column strength to be able to be maneuvered or actuated in the proximal or distal direction. Alternatively, the expandable scaffolding 802 can be used without a sheath 624 can be made of self expanding material such as NITINOL and in a way similar to that of FIGS. 1–6 with the additional benefit of having intermittent baskets.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof. For example, the present invention may be used in urinary drainage and abscess drainage in addition to the venous drainage applications described above.

What is claimed is:

1. An expandable venous cannula comprising:
   a tubular body having a length, a proximal opening, a plurality of distal ports located on a distal portion of said tubular body and a fluid lumen connecting said proximal opening to said plurality of distal ports, said fluid lumen being sized and configured to communicate fluid from a vein to an external cardiopulmonary bypass system;
   a scaffolding having a distal end and a proximal end coupled at its distal end to said tubular body having an expanded condition and a retracted position, said scaffolding surrounding said distal portion of said tubular body and said plurality of distal ports, said scaffolding being configured, when in the expanded condition to support an inner surface of the vein and prevent occlusion of said plurality of distal ports thereby facilitating fluid flow between the vein and said plurality of distal ports, wherein said scaffolding comprises a multiplicity of filaments arranged in a braided configuration, which is sized and configured to support the inner surface of the vein when in the expanded condition; an actuation member coupled to said distal end of said scaffolding.

2. The expandable venous cannula of claim 1, wherein said scaffolding has a length greater than its width.

3. An expandable venous cannula comprising:

a tubular body having a length, a proximal opening, a plurality of distal ports located on a distal portion of said tubular body and a fluid lumen connecting said proximal opening to said plurality of distal ports, said fluid lumen being sized and configured to communicate fluid from a vein to an external cardiopulmonary bypass system;

a scaffolding having a distal end and a proximal end coupled at its said distal end to said tubular body having an expanded condition and a retracted condition, said scaffolding surrounding said distal portion of said tubular body and said plurality of distal ports, said scaffolding being configured, when in the expanded condition to support an inner surface of the vein and prevent occlusion of said plurality of distal ports thereby facilitating fluid flow between the vein and said plurality of distal ports; and an actuation member coupled to said distal end of said scaffolding and slidable within said tubular body configured to radially expand said scaffolding.

4. The expandable venous cannula of claim 3, wherein said scaffolding comprises a multiplicity of filaments arranged in a braided configuration, which is sized and configured to support the inner surface of the vein when in the expanded condition.

5. The expandable venous cannula of claim 3, wherein said scaffolding has a length greater than its width.

6. The expandable venous cannula of claim 3, wherein said scaffolding is comprised of at least one strand member.

7. The expandable venous cannula of claim 3, wherein said scaffolding is comprised of a plurality of wires.

* * * * *